United States Patent [19]

Strohbeen et al.

[11] Patent Number: 4,610,681
[45] Date of Patent: Sep. 9, 1986

[54] DISPOSABLE UNDERPANTS HAVING DISCRETE OUTER SEALS

[75] Inventors: David T. Strohbeen, Outagamie County; John I. VanDeurzen, Winnebago County, both of Wis.

[73] Assignee: Kimberly-Clark Corporation, Neenah, Wis.

[21] Appl. No.: 740,135

[22] Filed: May 31, 1985

[51] Int. Cl.⁴ ............................................ A61F 13/16
[52] U.S. Cl. .................................................... 604/396
[58] Field of Search ............... 604/396, 365, 366, 370, 604/378, 385; 2/400

[56] References Cited

U.S. PATENT DOCUMENTS

| | | | |
|---|---|---|---|
| 2,834,347 | 5/1958 | Connally | 604/360 |
| 3,599,640 | 8/1971 | Larson | 604/397 X |
| 4,205,679 | 6/1980 | Rerke et al. | 604/366 |
| 4,337,771 | 7/1982 | Pieniak et al. | 604/365 |

*Primary Examiner*—John D. Yasko
*Attorney, Agent, or Firm*—Paul A. Leipold; Donald L. Traut; J. J. Duggan

[57] ABSTRACT

The invention is generally accomplished by providing a disposable undergarment having a multi-layer web and sealed with small, neat, exterior seams. The exterior seams are sealed along a plurality of narrow lines such that the total seam is less than about 3/16" wide with the bonding area forming about 50% of said total seal area. The seam is preferably formed by means of an ultrasonic anvil.

23 Claims, 7 Drawing Figures

DISPOSABLE UNDERPANTS HAVING DISCRETE OUTER SEALS

TECHNICAL FIELD

This invention relates generally to the field of disposable underpants having elasticized leg and waist openings, particularly disposable infant's training pants and similar garments.

BACKGROUND ART

Disposable diapers, as is well known, now find widespread use for infant care and have generally replaced the use of cloth diapers. The typical disposable diaper is a three-layer composite structure comprising a liquid permeable bodyside inner liner, a liquid impermeable outer cover and an absorbent batt sandwiched between the liner and the cover. Materials now in general use for the three principal elements of a disposable diaper include various types of nonwoven fabrics for the bodyside liner, a thin thermoplastic film for the outer cover and cellulosic fluff for the absorbent batt.

Disposable diapers of the type presently on the market are flat open-sided garments that are intended to be fit about an infant by a parent while the infant is lying down. The rear panel of the diaper is placed underneath the infant, and the front panel drawn between the infant's legs, after which the sides are overlapped and held together by pressure-sensitive adhesive tape. A diaper is meant for use when the child is young and dependent upon a parent for this essential purpose.

The popularity of disposable diapers has led to the belief that there is a demand for a disposable underpant, such as a disposable training pant, that can be used when a child grows out of a diaper. Diapers are typically used with infants up to about fifteen months old. When a child reaches an age in the range of about fifteen to thirty months, however, a parent generally desires to start toilet training so that the child can become independent of a parent. The training pant is intended for use when the child has reached an age at which he or she is ready to graduate to an underpant type of garment as a replacement for disposable diapers previously used. Thus, a suitable training pant must be a garment having closed sides so that a child can raise and lower it as necessary without requiring the aid of a parent. At the same time, a training pant must provide features of liquid and solid absorbency and prevent leakage of the waste fluids.

Cloth training pants, although widely-used, have disadvantages. Current cloth training pants have very little absorbency and often must be used with exterior rubber or plastic pants. When a child wets a cloth training pant, most often all of the child's clothes must be changed. Further, if a child has a bowel movement, it is difficult to remove a cloth pant without making a mess, and the pant must be soaked and bleached. All of these factors can make the toilet training process frustrating for both child and parent.

In addition, it is believed that the psychology of the toilet training stage is such that the child should perceive he or she is graduating to a garment that is different than a disposable diaper. The requirements for a disposable underpant such as a training pant are not satisfactorily met by the constructions of disposable diapers as currently known in the art. In this connection, for example, the typical disposable diaper, as stated previously, has an outer layer comprising a liquid-impermeable sheet of plastic film. Various techniques have been used to give the plastic sheet the feel and appearance of texture, but the exterior of the garment has a plastic feel or appearance which is closely associated with the concept of a diaper but would be inappropriate for a disposable training pant. Since the purpose of a training pant is to encourage the child to make the transition from diapers to washable or reusable cloth underpants, it is important that a disposable training pant simulate a cloth underpant as much as possible.

There has been proposed a particular desirable disposable underpant in U.S. Ser. No. 690,351, filed Jan. 10, 1985, with Inventors Heran et al. This disposable underpant while particularly desirable has a complication in its formation as the side seals are on the interior of the garment. The formation process involves the necessity of formation of the garment with the interior facing outward for side sealing after which the garment is reversed prior to packaging for sale. Reversing of the completed elasticized garment is an extra mechanical handling step that it would be desirable to eliminate as it is complicated and expensive. However, generally undergarments have been formed with inner side seams seals as the looks is improved by not having flaps on the outer surface. Further, the turning of the flaps to the inside of the garment has created additional difficulties in that the inside seals can be a source of skin irritation unless they are carefully formed. On the other hand, if exterior conventional seals are formed, they create flaps that have an undesirable appearance as it is intended that the garments resemble cloth underpants which do not have exterior seams. Therefore, there is a need for an exterior seal on a disposable garment that is discrete, strong, and easy to form.

DISCLOSURE OF THE INVENTION

An object of this invention is to overcome disadvantages of prior disposable underpants.

A further object of this invention is to create a discrete side seal for disposable garments.

A further object of this invention is to simplify the manufacture of disposable undergarments.

A further additional object of the invention is to provide strong garment side seals.

These and other objects of the invention are generally accomplished by providing a disposable undergarment having a multi-layer web and sealed with small, neat, exterior seams. The exterior seams are sealed along a plurality of narrow lines such that the total seam is less than about 3/16" wide with the bonding area forming about 50% of said total seal area. The seam is preferably formed by means of a ultrasonic anvil.

MODES FOR CARRYING OUT THE INVENTION

The side seam of the invention is particularly advantageous for disposable garments where low cost formation is particularly desirable. The side seal of the invention is strong and further the seal is particularly effective for multi-layered garments, even providing seam adhesion when elastic is within the seam. Further, the multi-line bond provides a higher bond strength than one large seal at the edges. The multi-line sealing provides an attractive almost invisible edge. The formation of the outer seal does not provide a seam on the inside of the garment to irritate the wearer. These and other advantages will be apparent from the detailed description below.

Figure 1:
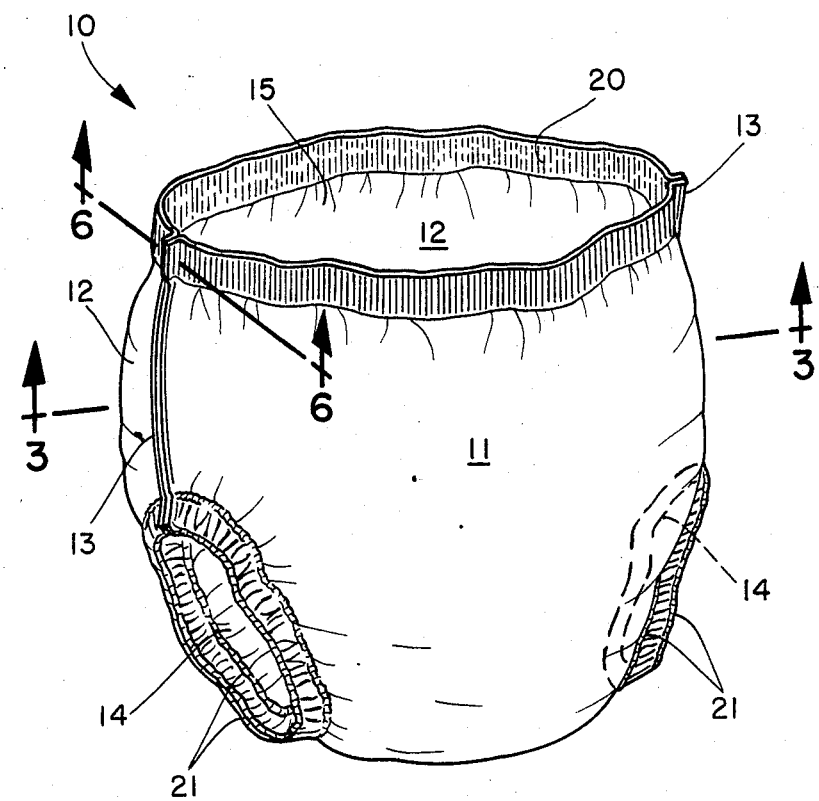
FIG. 1 is a perspective view of a disposable underpant according to the present invention.
Figure 2:
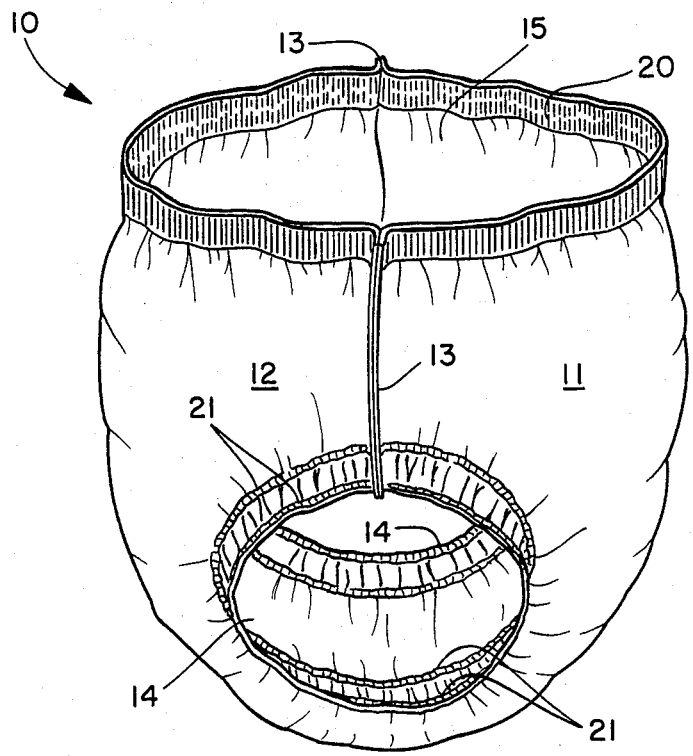
FIG. 2 is a side perspective view of the disposable underpant of FIG. 1.
Figure 3:
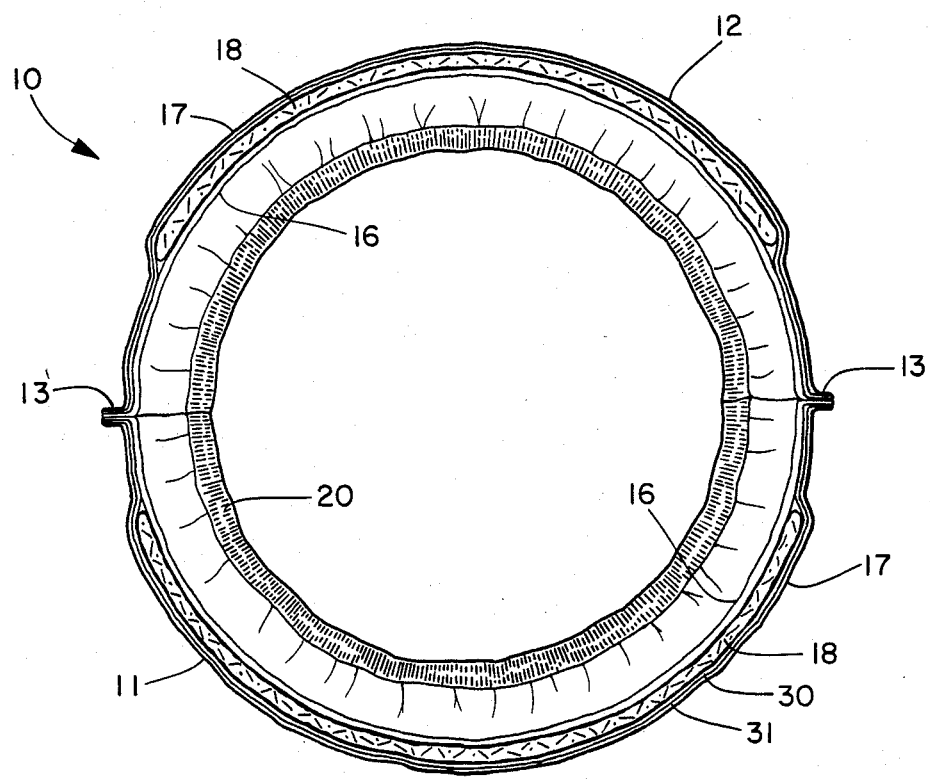
FIG. 3 is a horizontal sectional view of the disposable underpant of FIG. 1.

FIGS. 1 and 2 illustrate, in front and side perspective views respectively, a disposable underpant 10 constructed in accordance with the present invention. The underpant 10 includes a front panel 11 and a rear panel 12 joined together alongside exterior seams 13 to form a three-dimensional garment with closed sides having a pair of leg openings 14 and a waist opening 15. Referring now to FIG. 3, the underpant 10 includes a moisture pervious bodyside liner 16, a moisture impervious outer cover 17, and an absorbent batt 18 positioned between the liner 16 and outer cover 17. The absorbent batt may be secured to either the bodyside liner or the outer cover, or both, by any suitable means well known in the art such as lines or other patterns of adhesive, pressure sensitive tapes, heat seals, sonic seals, etc.

The waist opening 15 of the underpant 10 is surrounded by a circumferential elasticized band 20 and each leg opening 14 is surrounded by a circumferential elasticized band 21. Suitable constructions for the elasticized bands 20 and 21 are described in further detail later in this description.

The bodyside liner 16 can be any flexible porous sheet which passes fluids therethrough; i.e., a moisture pervious material, to be absorbed by the absorbent batt 18. The liner may comprise a nonwoven web or sheet of polyolefin fibers, such as polypropylene or polyethylene, or polyester fibers; a web of spunbonded polypropylene, polyethylene or polyester fibers; a web of rayon fibers; a bonded carded web of synthetic or natural fibers, or a mixture of synthetic and natural fibers, and the like. Further, the liner 16 may also comprise a plastic film which is perforated or apertured to obtain the desired degree of moisture perviousness, and may also comprise an expanded plastic webbing material or a scrim material. The bodyside liner 16 preferably is made of a material which will feel soft and comfortable against the skin of an infant or adult.

The absorbent batt 18 may comprise any suitable material capable of absorbing and retaining waste fluids that pass through the liner 16. Thus, the absorbent batt may comprise cellulosic material such as an air-formed batt of wood pulp fibers, commonly known as "fluff"; a batt of meltblown synthetic fibers, such as macrofibers or microfibers, of polypropylene, polyethylene, polyester and the like; a bonded carded web of synthetic or cellulosic fibrous materials; a composite of meltblown fibers, such as macrofibers or microfibers of polypropylene, polyethylene polyester or the like mixed with pulp fibers; or a blend of fluff with staple textile fibers such as rayon and the like. The batt may comprise one or more layers or combinations of the foregoing materials. In addition, the batt may include compounds added to increase its absorbency. The material selected for the absorbent batt most usefully has an absorbent capacity in the range of about 30 to 450 grams of synthetic urine retained at 0.5 psi. For a disposable training pant intended for infant use after the diaper stage, the absorbent capacity of the batt is preferably in the range of about 350 to 400 grams of synthetic urine retained at 0.5 psi. Furthermore, it is desirable that the underpant 10 not present a diaper appearance, and the absorbent batt, therefore, most usefully comprises a low-bulk, high-absorbency material.

In accordance with a preferred garment of this invention, the outer cover 17 performs the dual functionality of providing moisture imperviousness and also providing a textile feel and look for the underpant 10. For this purpose, referring now to FIG. 3, the outer cover 17 comprises a two-layer composite material having an inner layer 30 and an outer layer 31. The inner layer 30 is a layer or stratum of polymer material which provides a moisture barrier or liquid imperviousness. Suitable polymer materials for the inner layer 30 are polyolefin polymers such as polyethylene or polypropylene; polyolefin copolymers such as ethylene vinyl acetate, ethylene methyl acrylate or ethylene ethyl acrylate; polyvinyl chloride; nylon; or other thermoplastic materials capable of providing liquid imperviousness. The inner layer 30 of the outer cover should provide a sufficient degree of liquid imperviousness to prevent or preclude waste fluids from striking through or penetrating through the outer cover. The outer layer 32 of the cover 17 most preferably consists of a layer of nonwoven fibrous material. Materials suitable for the outer layer 31 include a spunbonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spunbonded nonwoven web or synthetic fibers such as polypropylene, polyethylene or polyester fibers mixed with cellulosic, pulp fibers or textile fibers; or meltblown thermoplastic fibers, such as macrofibers or microfibers, of polypropylene, polyethylene, polyester or other thermoplastic materials or mixtures of such thermoplastic macrofibers or microfibers with cellulosic, pulp or textile fibers.

The inner layer 30 and outer layer 31 of the cover 17 are advantageously bonded to one another, by any means appropriate for the specific materials selected for the two layers. The two layers can be laminated using heat or pressure or both heat and pressure. The two layers can also be bonded with adhesive, heat sealing or ultrasonic sealing. In addition, thermoplastic polymeric material of the inner layer 30 can be extrusion coated onto the nonwoven outer layer 31. If desired, the textile effect of the nonwoven outer layer 31 can be further enhanced by various embossing patterns.

FIG. 3 illustrates one form of exterior side seams 13 for the underpant 10 that is made by seaming together exterior contacting side edge portions of the outer layer 31 of the outer cover 17 of the front and rear panels. This provides a narrow fin seam, which is made relatively narrow so as to minimize the amount of seam visible. The seams 13 between the outwardly contacting side edge portions of the outer cover can be formed by any suitable means appropriate to the specified material employed for the outer layer 31 of the cover.

Figure 4:
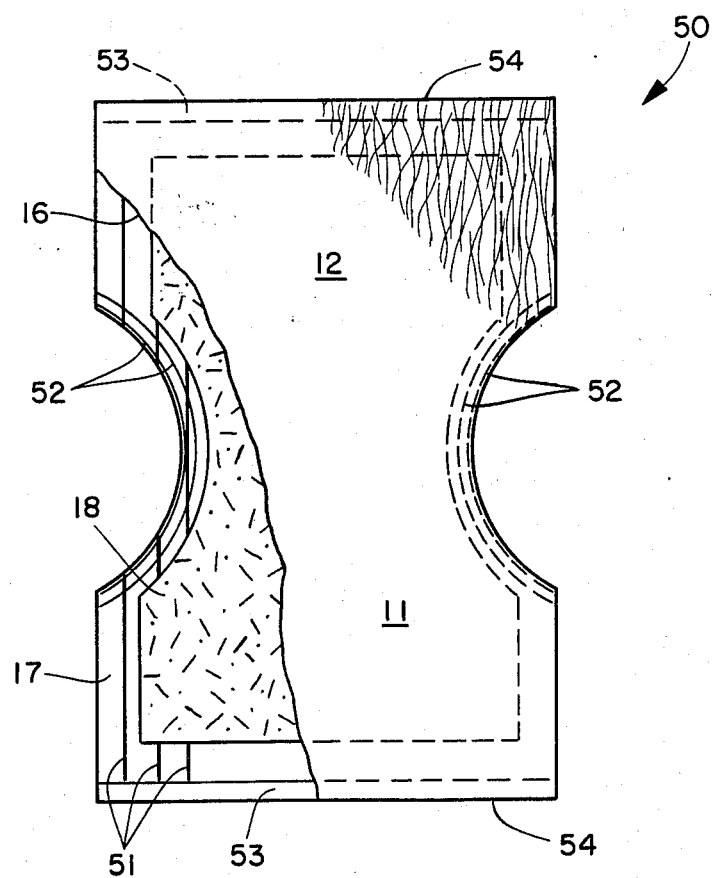
FIG. 4 is a plan view, with portions broken away illustrating a flat bank as suitable for producing the underpant of FIG. 1.

The underpant 10 can be expeditiously manufactured from a blank cut to a suitable configuration. An appropriate blank 50 is illustrated in FIG. 4. A sheet of material for the outer cover 17 is cut to an hourglass configuration having arcuate cutouts defining the leg openings of the garment. Absorbent batt 18, also cut to an hourglass configuration with arcuate leg cutouts, is placed on top of the outer cover in the desired position, and may be secured thereto by spaced parallel glue lines 51. An arcuate elastic means 52 is positioned around each leg cutout and preferably, as explained below, positioned along the outer edge of the cover 17 along the cutout portion. Linear elastic means 53 are positioned along each end 54 of the blank, which will form the elastic means for the waist portion of the finished garment. As indicated in FIG. 4 the elastic means 52 is positioned closely adjacent the nearby edge of the absorbent batt so as to provide a form-fitting panty type of garment instead of being spaced from the batt to have a web of material between the elastic means and the batt as is common with some disposable diapers. Next, a sheet of bodyside inner liner 16, also cut to an hourglass configuration, is placed over the assembly of the outer cover and the batt. Both the liner 16 and cover 17 have superimposed marginal portions which project beyond the margin of the batt 18, and the liner and cover may be joined together along glue lines 51 within the superimposed marginal portions. Also, the liner 16 is joined to the elastic means 52 and 53 along the edge portions of the liner in contact therewith. After being fully assembled, the blank 50 is folded along its central transverse area and the sides of the front and rear panels are seamed together as illustrated in FIG. 3 to form the finished underpant 10.

Figure 5:
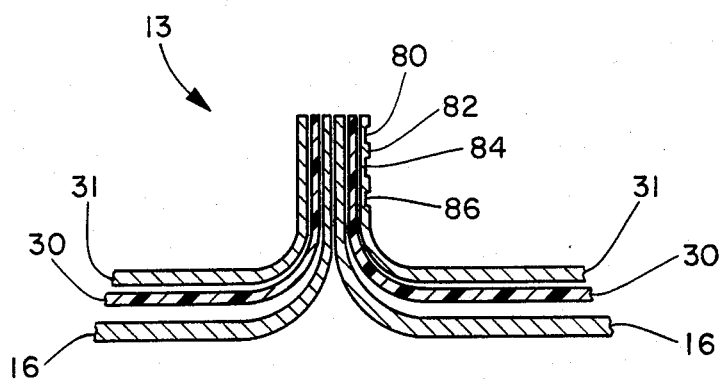
FIG. 5 is a sectional view of a side seam in accordance with the invention.

FIG. 5 is an enlarged view of the cross-sectional view of seam 13 in FIG. 3. The seam is composed of a six-layered structure of the outer fabric layer 31, the inner impermeable layer 30 of the cover sheet, as well as the permeable layer 16 forming the liner of the garment. Therefore, the seal 13 has six layers, all of which must be sealed together to form a small unobtrusive bond. This is done by sealing with a series of lines 80 that form the pressured areas 80 and raised lined areas 82. The sealing is accomplished within a preferred width of about ⅛" with a plurality of sealing lines being formed within this space. As illustrated, there are three sealing lines 80, 84, and 86 within the seal 13. Surprisingly, it has been found that the multi-line sealing carried out with ultrasonic sealing is stronger when a series of narrow lines are formed rather than a larger continuous sealed area.

The series of seal lines may be formed by any desired method. Typical of such methods are adhesive and heat sealing. A particularly preferred system for the invention is found to be ultrasonic sealing. It has been found that an ultrasonic sealing anvil having a plurality of lines closely spaced together such that four sealing lines may be fit within the preferred space of between ⅛ and 3/16" is particularly desirable. The sealing lines may be discontinuous, forming dashed lines.

In formation of the lines an ultrasonic apparatus suitable is a Branson 851 Model ultrasonic Sealing Unit and with a preferred anvil of ⅛" width and 6.0" length having engraved thereon a line pattern of about 0.45 mm wide lands and valleys about 0.35 mm wide forming four lines in a total width of about ⅛". This anvil is suitably applied with 350–1700 psi force for 0.05–2.0 seconds to the composite forming the side seal of the garment to laminate the front and back portions together. The preferred anvil force is about 400–600 psi force for about 3 seconds.

Figure 6:
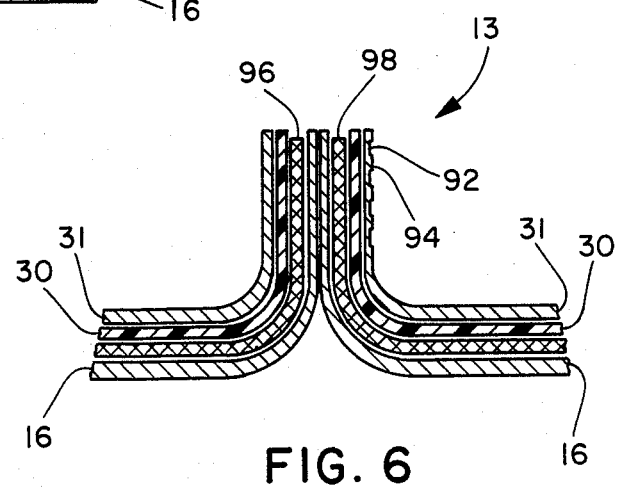
FIG. 6 is a side perspective view of an alternate form of the disposable panty of FIG. 1.

Illustrated in FIG. 6 is a cross section of the garment 10 taken on section line 6 of FIG. 1 such that the cross-section of the seam 13 is taken at the waist elastic. Surprisingly it has been found that the ultrasonic sealing forming a pattern of sealed valleys 92 and raised lines 94 between the valleys even seals in this area where the front and back waist elastic 96 and 98 are present in the seam.

Figure 7:
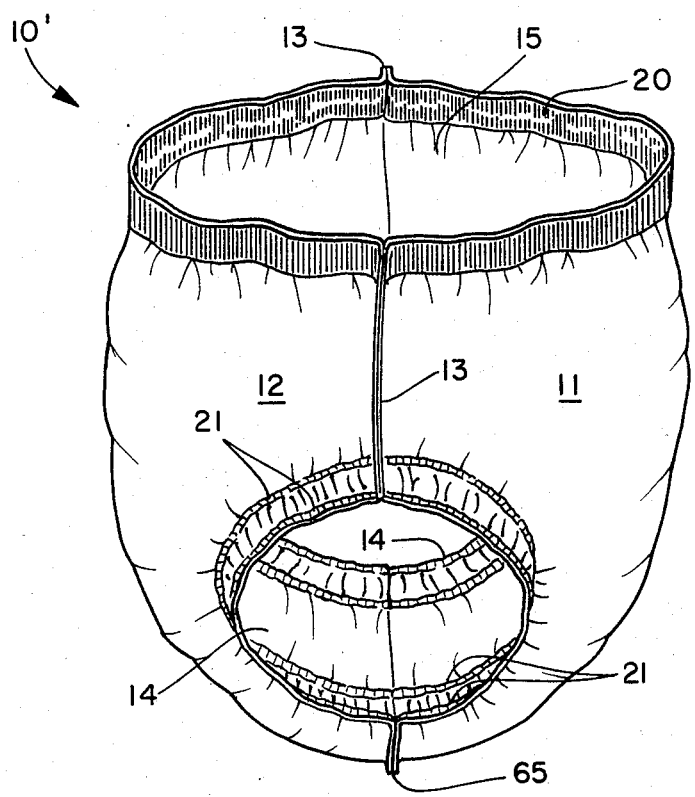
FIG. 7 is a sectional view of a side seam at the waist of a disposable underpant in accordance with the invention.

FIG. 7 illustrates an alternate system for construction of the underpant of the present invention wherein the underpant 10' includes a separate front panel 11 and rear panel 12 that are joined together along central crotch seam 65. The remaining elements of the underpant 10' are the same as in underpant 10 and the common elements are identified with the corresponding reference numerals employed in FIG. 1. FIG. 7 represents an alternative method for constructing the underpants of the present invention as compared to making the underpants with the folded blanks 50 of FIG. 4.

The discrete, strong, nonleaking side seal of the invention may be formed in any desired width. Generally the seam would have a width of between about 1/16" and about 3/16". It is preferred that the seam have a total width of about ⅛". Within the seam area encompassed by the lines of sealing in the seam's bonding area the sealed valley portions are generally about 25% to about 100% of the total. The number of lines may be any desired number greater than 1. Generally is has been found that four sealing lines in a space of about ⅛" with about 50% seal area are suitable.

Any suitable elastomeric material can be employed for the elastic in the garments of the invention that exhibits at least an elongation (defined herein as $L_s - L_r/L_r$ where $L_s$ is the stretched length of an elastic element and $L_r$ is retracted length, multiplied by 100 to obtain percent elongation) in the range of 5% to 300% preferably in the range of 25% to 200%. Further along these lines, there may be some preferential vagaries in respect of the elasticity of these elastic means relative to the geometry elected by the designer. For example, within the preferred range mentioned above, it has been determined that a most preferred range of from about 40% to about 150% is advantageously associated with ribbon elastic (e.g., elastic means 52 and/or 53) while a most preferred range of from about 75% to about 175% is advantageously associated with rope elastic elements. Various commercially-available materials can be used, such as natural rubber, butyl rubber or other synthetic rubber, urethane elastomeric material such as that available from B. F. Goodrich Company under the trademark TUFTANE, and elastomeric material available from the H. B. Fuller Company under the tradename FULLASTIC. The latter material (see e.g. U.S. Pat. No. 4,418,123) is based upon thermoplastic elastomeric copolymers of the A-B-A type such as those available from Shell Chemical under the trademark KRATON which have a rubbery midblock such as butadiene or isoprene and polystyrene end blocks, and is especially useful because it is a self-adhesive material and can be applied to the layers of the garment without additional adhesive between the elastic means and the layers. The elastic means can be applied to the garment by any suitable means including adhesive bonding, heat sealing or sonic bonding, whichever is appropriate to the specific material selected for the elastic means.

EXAMPLE

A disposable panty 10 as illustrated in FIG. 1 was constructed in a size suitable for use as an infant's training panty with an elasticized waist opening as shown in FIG. 1. The material of the outer cover, or exterior panel, of the disposable underpant was a two-layer composite web having an outer layer of nonwoven polypropylene fibers and an inner layer of ethylene methyl acrylate extrusion coated onto the nonwoven fibrous outer layer. The panty had an interior panel comprising a bodyside liner of spunbonded polypropylene microfibers and cellulosic fiber absorbent was sandwiched between the exterior panel and the interior panel. The exterior seams were sealed ultrasonically with a series of 4 lines within a side seal of about ⅛". Testing of the panty established that it combined the features of liquid imperviousness due to the plastic inner layer of the outer cover and a cloth-like appearance because of the fibrous outer layer of the outer cover. The sealing of the side seal seams was strong and complete and did not detract from the panty-like appearance of the garment. A useful disposable training pant was thereby provided that is expected to be well-received by parents and of a type that will aid and encourage children going through the toilet training stage.

There has thus been described a preferred disposable underpant including an outer cover constructed of two layers of different materials wherein the inner layer is a plastic material capable of providing the desired degree of moisture imperviousness and the outer layer is a nonwoven fibrous material capable of presenting a clothlike or textile appearance and feel to the underpant. The garment further has an exterior side seal seam that is capable of holding the garment together without being obtrusive. It is believed that the new garment seal herein described provides a construction that is an improvement over similar garments of the prior art.

The outside seal seam of the invention is particularly desirable when composite materials containing spunbonded material such as polypropylene or polyethylene are present. In the illustration set forth above the sealing system was satisfactory for sealing even when eight layers including adhesive layers were present. It is particularly desirable for a multi-layer sealing of thermoplastic materials. The seal of the invention is stronger than a single large seal and additionally the line structure does not detract extensively from the cloth-like outer surface of the spunbonded surface on the garment illustrated.

While the invention has been specifically described with respect to training pants, other types of garments may also be formed by the sealing system of the invention utilizing an ultrasonically-sealed narrow seam having a plurality of lines of sealing. Other garments that the seal could be used for are training pants that have absorbent inserts rather than the disposable pants illustrated. Other garments to benefit by the side seam of the invention could be disposable bathing suits. The invention is also suitable for hospital garments such as gowns, as well as hospital underwear. Further, the invention could be utilized in formation of cloth-like bags, and particularly is suitable for formation of cloth-like disposable bags as it is easier to make them using the system of the invention as the garment or bag does not need to be turned inside out after formation.

The present invention has been described hereinabove by reference to several specific embodiments, but it is expected that those skilled in the art of manufacturing disposable garments will be able to devise modifications of the exemplary embodiments and it is intended that the appended claims encompass any such obvious modifications which are within the true spirit and scope of the present invention.

I claim:

1. A disposable garment comprising a multilayer web and at least one sealed exterior seam formed by bringing the inner surfaces of multilayer webs at their respective edges into contact such that the resulting seam extends outwardly from the garment and wherein said at least one seam is sealed with at least two narrow lines, the total seam is less than about 3/16" wide.

2. The garment of claim 1 wherein said multilayer web comprises at least two layers of spunbonded web and one layer of polymer sheet.

3. The garment of claim 1 wherein said seams are sealed across the waist elastic.

4. The garment of claim 1 wherein said sealing is ultrasonic.

5. The garment of claim 1 wherein said seam is about ⅛" wide and bonded on about 50% of said total seam area.

6. The garment of claim 1 wherein said seam is also at an elastic leg and elastic waist.

7. The garment of claim 1 wherein said at least one seam comprises an ultrasonically-sealed seam at each side of said garment.

8. The garment of claim 7 wherein said outer cover comprises a spunbonded polypropylene web bonded to a polymer film, an inner spunbonded garment liner and an absorbent member between said outer cover and said inner liner.

9. The garment of claim 8 wherein said ultrasonically-sealed side seams comprise four lines of ultrasonic sealing in a seam about ⅛" wide.

10. A method of forming an exterior seam in a garment comprising bringing together at least two webs of multiple layer material, such that the inner surfaces of said webs at their respective edges are joined and the resulting seam extends outwardly from said garment, sealing said materials together along at least two narrow lines forming a seal less than about 3/16" in width.

11. The method of claim 10 wherein said sealing is performed ultrasonically.

12. The method of claim 11 further including sealing across the elastic.

13. The method of claim 11 wherein said seam is formed ultrasonically and is about ⅛" wide.

14. The method of claim 11 wherein said seam comprises four narrow sealing lines.

15. The method of claim 11 wherein said sealing is by an ultrasonic anvil of ⅛" width applying about 400 to 600 psi pressure to said garment.

16. The method of claim 15 wherein said anvil has a surface of 4 parallel lands about 0.45 mm wide separated by valleys about 0.35 mm wide.

17. The method of claim 11 wherein said seam is about ⅛" wide and comprises four sealing lines.

18. The method of claim 11 wherein said lines are discontinuous.

19. The method of claim 18 wherein said at least two lines comprise four lines.

20. A disposable underpant of the type having a liquid-pervious inner bodyside liner and a liquid-impervious outer cover that define a front panel and a rear panel, and an absorbent batt between the liner and the cover, comprising, in combination:
(1) narrow exterior side seams joining together part of marginal side portions of the front and rear panels to define a three-dimensional underpant having a pair of leg openings and a waist opening, said narrow exterior seams being formed by joining the inner surfaces of the front and back panels at their respective edges such that the resulting seam extends outwardly from the garment;
(2) first elastic means extending about one leg opening, second elastic means extending about the other leg opening, and third elastic means extending about the waist opening; and
(3) the outer cover consisting of an inner layer of liquid-impervious plastic material and an outer layer of nonwoven fibrous material, wherein the inner layer faces the absorbent batt, and the outer layer is the exterior surface of the disposable underpant.

21. A disposable underpant according to claim 20, wherein: the exterior side seams join together outward extending side edge portions of the front and rear panels about $\frac{1}{8}''$ in width.

22. A disposable underpant according to claim 20, wherein: the side seams comprise a bond portion in the range of 1/16" to 3/16" wide.

23. The underpant of claim 20 wherein said seams are sealed ultrasonically.

* * * * *